United States Patent [19]

Seitz

[11] 4,158,126
[45] Jun. 12, 1979

[54] HEATING UNIT FOR DISINFECTING SOFT LENSES, OR THE LIKE

[76] Inventor: Lamont J. Seitz, 9302 Candlewood Dr., Huntington Beach, Calif. 92646

[21] Appl. No.: 834,104

[22] Filed: Sep. 19, 1977

[51] Int. Cl.$^2$ .............................................. F27D 11/02
[52] U.S. Cl. ..................... 219/439; 422/307; 219/386; 219/214; 219/328; 219/430; 219/441; 219/521
[58] Field of Search ............... 219/214, 430, 429, 437, 219/433, 438, 439, 441, 442, 521, 523, 513, 530, 385, 386, 387, 327, 328; 21/89, 92, 119, 120; 337/112

[56] References Cited

U.S. PATENT DOCUMENTS

| | | | |
|---|---|---|---|
| 2,236,837 | 4/1941 | Rimmel | 219/439 X |
| 3,130,288 | 4/1964 | Monaco et al. | 219/385 |
| 3,294,039 | 12/1966 | Ogden | 219/439 X |
| 3,432,642 | 3/1969 | Lohr et al. | 219/439 |
| 3,764,780 | 10/1973 | Ellis | 219/430 |
| 3,805,018 | 4/1974 | Luong et al. | 219/387 |
| 3,851,861 | 12/1974 | Cummins et al. | 219/328 X |
| 3,931,494 | 1/1976 | Fisher et al. | 219/441 |
| 3,961,893 | 6/1976 | Russell et al. | 21/92 X |
| 3,998,590 | 12/1976 | Glorieux | 21/89 |
| 4,041,433 | 8/1977 | Watson | 219/328 X |

*Primary Examiner*—Volodymyr Y. Mayewsky
*Attorney, Agent, or Firm*—Keith D. Beecher

[57] ABSTRACT

A heating unit which may be used as a soft contact lens disinfecting unit and which embodies a case construction entirely of thermoplastic, or other low heat-conductive material. A heat conductive liquid such as molten wax, or oil, or both, is contained in the case and is used as a uniform heat transfer medium between electrical heating elements in the case and the surface of an incubator supported in the case which, likewise, is formed of low heat-conductive material. The heating unit in the embodiment to be described, is specifically constructed to produce or aid in disinfecting so-called soft contact lenses intended for wearing in contact with the eye. The unit is more generally applicable, and may be used to advantage, when a low cost heating unit is desired which will raise the temperature of an object or a material to a given temperature, maintain it at or above the given temperature for a given time period, and then allow it to cool down and return to an ambient temperature condition.

5 Claims, 6 Drawing Figures

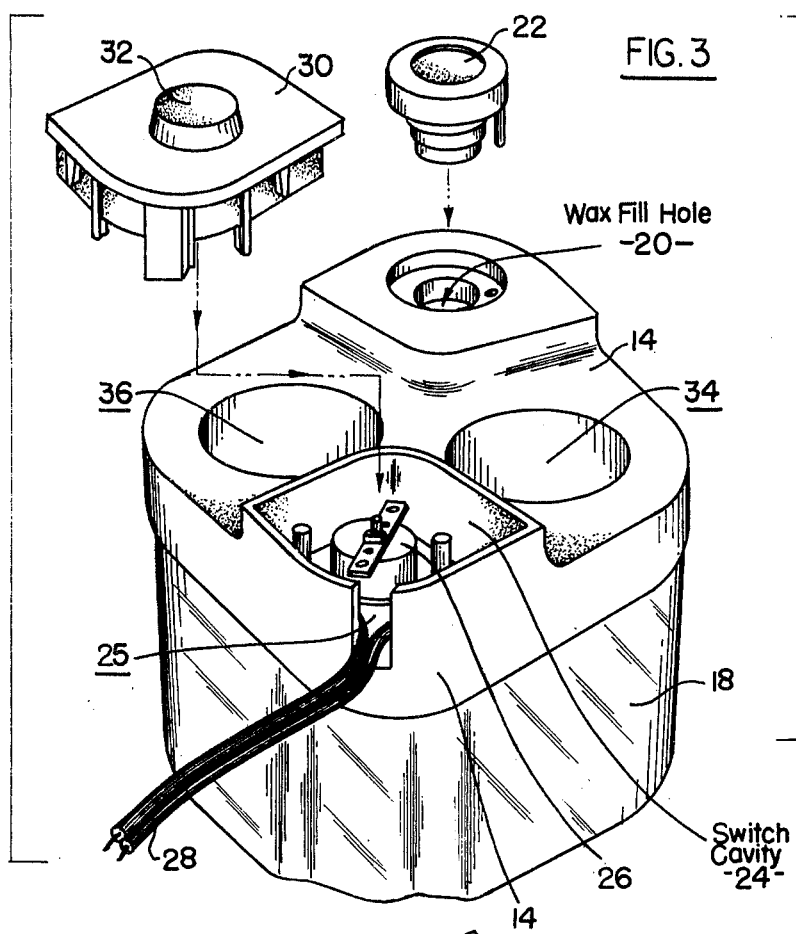
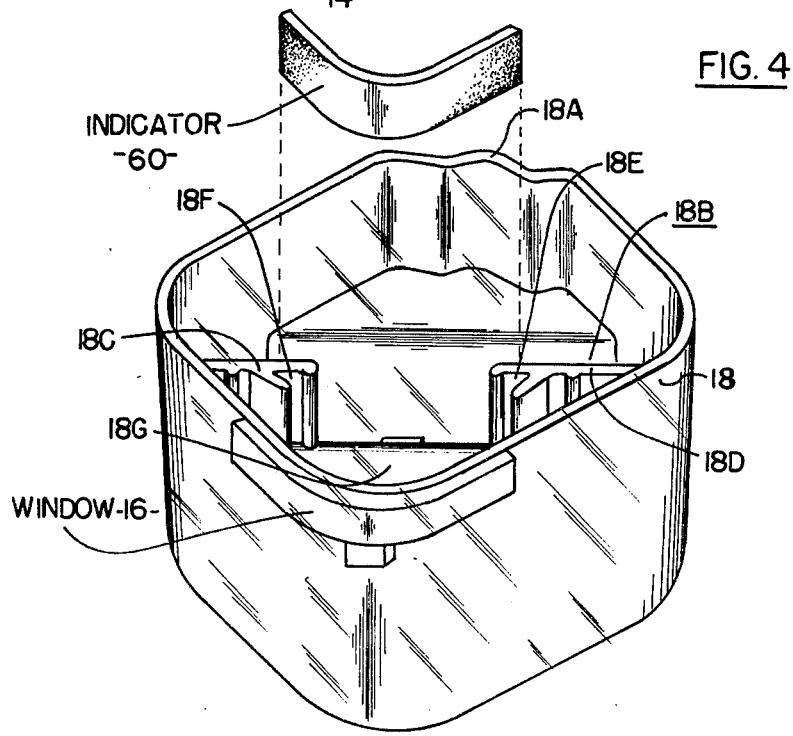

HEATING UNIT FOR DISINFECTING SOFT LENSES, OR THE LIKE

BACKGROUND OF THE INVENTION

It is necessary to produce periodically an essentially disinfected condition in soft contact lenses so that bacterial organisms or their by-products will not cause harm to the wearer's eyes. Since the soft lens material is permeable to liquids, soaking the lens in strong germicidal solutions will result in the lens becoming impregnated with the solution, and this can lead to irritation to the user's eye when the lens is worn. In general, it has been found difficult to disinfect soft lens by treatment with chemical or biochemical solutions which will not cause eye irritation to at least some percentage of the wearers.

As an alternate means for producing the desired disinfected condition in the soft lens, heat may be used. The lens may be kept immersed in physiologically normal saline solution, or its equivalent, when it is not being worn, to prevent the lens material from drying out. Heat is therefore generally applied by first placing the lens in a suitable container or lens holder; adding a suitable amount of saline solution, of the proper concentration, so that the lens is totally immersed; closing or covering the lens container; placing the lens container in a suitable heating unit; and energizing the heat unit.

The heating unit must raise the temperature of the saline solution and immersed lens to the required temperature, hold the lens at or above this temperature for the required time, and then allow it to cool to ambient temperature. Typical values of the time and temperature deemed suitable for producing the disinfected condition require the lens to be maintained at or above 80° C., for a period of 10 minutes or more. Since aging of the lens material is accelerated by excessive temperatures and/or by extended time at elevated temperatures, it is desirable that the heating unit be controlled so that excessive temperatures, or excessive time at elevated temperatures, will not shorten the life of the lens.

The heating unit must be designed with careful attention to electrical safety/shock hazard considerations since the user typically uses the unit in a bathroom adjacent to grounded water piping and wash basins. Since the typical household electrical outlets are only two contact, without grounding pin provisions, it is impractical to use a 3-wire power cord with a ground connection to any exposed metallic portions of the device. The user of the prior art unit is therefore potentially subject to a significant shock hazard if he touches a grounded object such as a water faucet while in contact with any metallic portion of the heating unit. Any current leakage path between the electrical circuitry and the exposed metallic portion of the prior art unit can lead to potential fatal shock hazards under these conditions. It would therefore be very advantageous to have the heating unit constructed so that there is no exposed or exposable portion of the unit constructed of metal or other electrically conductive materials. The unit of the present invention is so constructed.

There are two general design approaches which have been used in the prior art to produce heating units for this type of application. The first is to incorporate a metallic heating block which has been configured to hold the lens container. An electrical heater in the form of a surface mounting flat heater mounted to a flat face of the block, or in the form of a tubular heater fitting into a hole or slot, is used to provide heat input to the block. A thermostatic switch, connected in series with the heater regulates the block temperature at some selected set point. The timing function is typically provided by a separate spring wound clock-work or motor driven timer. An overall plastic heating is usually used to provide thermal isolation for the metal heating block and to enclose the electrical components.

The disadvantages of the prior art construction described in the preceding paragraph are numerous. The metallic heating block requires relatively expensive precision casting and/or machining operations, as well as requiring added cost in painting or other finishing operations. The heating block provides a potential shock hazard should any electrical leakage develop between it and the electrical circuitry. It is difficult to provide a liquid tight seal between the metallic heating block and the plastic enclosure so that any liquid spilled or splashed in the use of the unit is likely to cause damage to, or current leakage in the unit. There is typically no way for the user to tell if the unit has reached its proper operating temperature. The cost of the timer incorporated into the prior art unit is appreciable and adds significantly to the relatively large manufacturing cost of this type of unit.

The heating element, either flat or tubular, is again of significant cost in the aforesaid prior art unit. Since the total timer cycle includes the time necessary to raise the heating block temperature to the regulating point of the thermostat, differences in input power due to heater resistance tolerances, or to variations in the applied power line voltage, will cause variations of the warm-up time and thus to the remaining time-at-tempeature cycle of the timer.

The second prior art design approach is again one where a metallic heating block is used. The configuration of the heating block is similar to that of the first approach and the same type of electrical heaters may be used. A thermally sensitive switch is mounted on the block and connected in series with the heater. The switch is manually actuated to energize the unit. The heating block serves as a conductive means to distribute the heat from the heating element to the lens and to the thermal switch. When the switch temperature reaches its preset actuating temperature, the switch opens and removes power from the heating element. The block temperature immediately starts decreasing towards the ambient temperature. As the block is being heated, a certain amount of heat energy is stored in the thermal capacity of the block. The mass of the block, its specific heat, and its temperature rise determine the amount of heat energy stored. The amount of stored heat, and the insulating factors of the block mounting in the usual plastic case, determine the rate of decay of the block temperature.

In order to maintain the lens temperature at or above a given value for a given time in the second type of prior art heating unit, it is usually necessary to allow the lens temperature to overshoot the desired value by an appreciable amount in order that sufficent time at or above the desired temperature can be realized.

All of the disadvantages of the metallic heating block mentioned in the first prior art unit apply equally to the second prior art unit. The heating element is again a siginificant cost factor. There is typically no way for the user to be certain that the second prior art unit has attained the proper temperature in use. Only a limited amount of heat energy can be stored in the thermal mass of the heating block of the second prior art unit so it is hard to maintain the lens at a more-or-less constant temperature.

OBJECTIVES OF THE PRESENT INVENTION

1. To provide a heating unit which does not require a metallic heating block with the attendant disadvantages of cost, difficulty of sealing, and potential shock hazard.

2. To provide a heating unit in which all of the exposed parts are composed of injection molded plastic parts, thus eliminating potential shock hazards; enabling easy, virtually hermetic sealing; enabling the unit to be readily cleaned to sanitary condition; and enabling the unit to be low in manufacturing cost.

3. To provide a heating unit which can use low cost power resistors for the heating elements, and thus save substantial manufacturing costs compared to conventional heating elements.

4. To provide a heating unit which is extremely economical in parts cost, as well as in assembly and fabrication labor costs.

BRIEF DESCRIPTION OF THE DRAWINGS

FIG. 3 is a perspective view of the unit of FIG. 2 removed from its housing;

FIG. 4 is a perspective view of a bowl portion of the unit of FIG. 3;

DETAILED DESCRIPTION OF THE ILLUSTRATED EMBODIMENT

Figure 1:
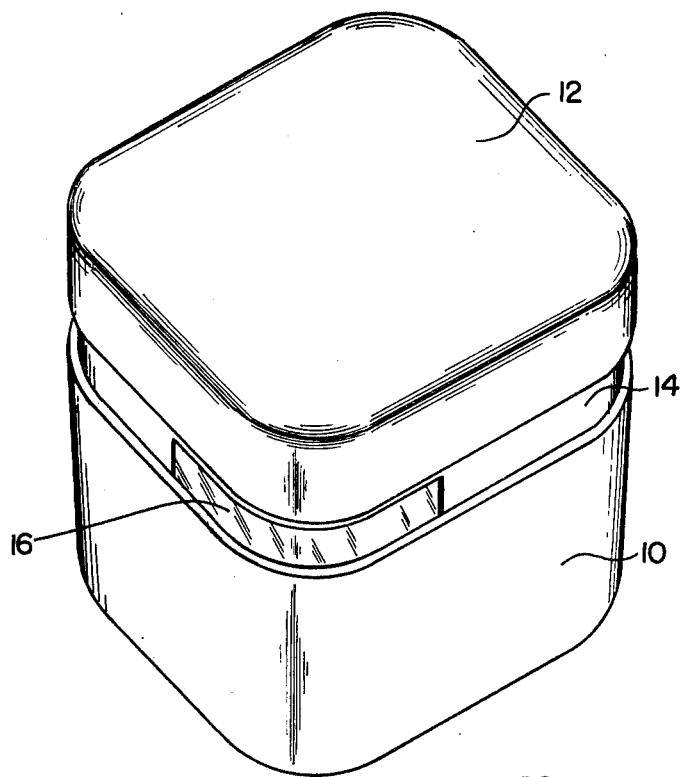
FIG. 1 is a perspective representation of a heating unit which may be constructed in accordance with one embodiment of the invention.

The heater unit of the invention, as shown in FIG. 1, for example, includes a housing 10, a cover 12, and an incubator 14, which fits into the housing, and which is enclosed by the cover. A window 16 is provided through which an indicator may be observed when the unit has reached its operating temperature. The incubator is supported in a bowl 18, as shown in FIG. 3. The housing 10 provides a more pleasing appearance for the unit, and serves especially to insulate the user against the high temperatures within the unit. The housing may be molded from a high operating temperature grade for opaque thermoplastic, such as polycarbonate.

An air space is provided between the inner wall of housing 10 and the outer wall of bowl 18. This air space acts as an insulating means and prevents the outer surface of housing 10 from reaching uncomfortable temperatures. The housing 10 is joined to bowl 18 preferably by ultrasonic welding to form a joint between the bottom edge of bowl 18 and the inside bottom surface of housing 10. The cover 12 serves to reduce heat loss in the unit during the disinfection cycle, and also serves to prevent dust and dirt from settling on the internal components of the unit.

The incubator 14 may be molded from an opaque high operating temperature grade of plastic such as polycarbonate. The incubator contains two wells 34 and 36 (FIGS. 2 and 3) of suitable dimensions to accept the maximum vial size to be used as lens holders during the heating/disinfecting operation of the unit. The top of the molded from constituting incubator 14 also contains a switch cavity 24 and a fill hole 20 (FIG. 3).

Figure 5:
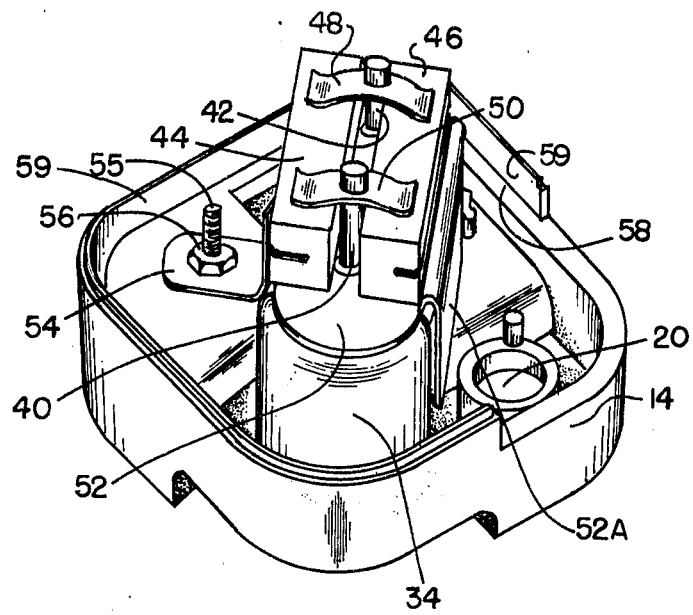
FIG. 5 is an inverted perspective view of an incubator portion of the assembly of FIG. 3 which fits into the bowl portion.

As shown in FIG. 5, the walls forming the bottoms of lens holder wells 34 and 36 have downwardly-extending molded elongated protrusions or posts 40 and 42. These posts are used as part of the mechanical assembly means. A flange 58 extends in a continuous plane around the entire inside of the incubator 14 at the base of a peripheral lip 59, as also shown in FIG. 5. The flange area 58 provides a flat surface for a plastic welding operation which joins the incubator 14 with the bowl 18.

Bowl 18 (FIG. 4) may be molded from a high operating temperature transparent plastic, such as polycarbonate. The bowl contains an outwardly extending flange which forms the window 16. Two indicator mounting walls 18C and 18D extend vertically and terminate in indicator mounting notches 18E and 18F. A recess 18B extends to the bowl bottom. The top edge 18A extends around the top periphery of bowl 18 in a continuous plate which ultimately mates with and is welded to flange 58 of incubator 14 (FIG. 5).

An indicator 60 (FIG. 4) which is molded or formed from high operating temperature plastic such as polycarbonate, is fitted into notches 18E and 18F. The color of the indicator is selected to be highly visible to the eye, and preferably is made to be some shade of red. Indicator 60 may be secured in the indicator mounting notches 18E and 18F of bowl 18 by the application of an appropriate plastic adhesive.

The bottom edge of indicator 60 fits closely against the surface of step 18G (FIG. 4). In conjunction with the indicator mounting walls 18C and 18D, the indicator forms a liquid-tight dam across step 18G. Liquid in the area between window 16 and indicator 60 is retained by the dam.

As will be described, bowl 18 is filled with molten wax or oil, or a combination of both, when the unit is operational. The dam formed by indicator 60 and indicator mounting walls 18C and 18D (FIG. 4) traps and retains the wax when the unit is hot and the wax is molten. As the wax solidifies, its volume decreases substantially. If it were not for the damming effect of indicator 60, the level of the solid wax in the unit could fall below the top of window 16, and thus allow part of indicator 60 to be visible when the unit is cold. The small amount of shrinkage in the wax trapped by the dam, prevents this from occurring.

The indicator 60, and its associated components form the subject matter of copending application Ser. No. 835,420 filed Sept. 21, 1977 in the name of John Bowen.

A manually resettable thermostatic switch 26 (FIG. 3) is mounted within the switch cavity 24. The switch is thermally coupled to the molten wax. The switch has an operating temperature higher than the melting point of the wax. This switch may be of the type manufactured by Elmwood Sensors, Inc. The switch is mounted in switch cavity 24 by means of a threaded mounting stud 55, which as shown in FIG. 5 protrudes through the bottom of the switch cavity 24. A notch 25 on the corner of switch cavity 24 provides an exit point for the electrical power cord 28 of the unit.

In order to provide a cover over the thermostaic switch 26 and the electrical connections in switch cavity 24, a switch cover 30 (FIG. 3) is provided. The switch cover 30 may be injection molded from an opaque grade of high operating temperature plastic such as polycarbonate. The cover contains a hole in its top surface, and a boot 32, which may be molded from a suitable high operating temperature elastomer such as Krayton, is mounted in the hole. Boot 32 provides a flexible cover for the operating push-button of switch 26, and allows operation of the push-button while sealing the switch cavity 24 against dust and moisture.

A heat pick-up member 54 is provided, in the form of a small metal angle member with a clearance hole for the mounting stud 55 of thermostatic switch 26, as shown in FIG. 5, and the heat pick-up member is held down by a nut 56 which is threaded to stud 55. The nut also holds the thermostatic switch 26 firmly against one face of the bottom wall of the switch cavity 24, as it holds the heat pick-up member 54 against the other face of the bottom wall, with the bent-over portion of the pick-up member lying alongside the side walls of lens holder wells 34 and 36.

An optional heat-conducting member 52 may also be provided as shown in FIG. 5, and this heat conducting member may take the form of a metal part having two holes whose diameter and center-to-center spacing allow the heat-conducting member 52 to fit over posts 40 and 42 of incubator 14. A portion of the heat-conducting member 52 may be bent at right-angles to form a fin 52A. The fin 52A if used, may lie along the side walls of the lens holder wells 34 and 36 on the opposite side to the heat pick-up member 54. The heat conducting member 52, if used, serves to slightly shorten the time required for the lens holders, inserted in lens holder wells 34 and 36, to reach the desired temperature.

FIG. 5 shows two resistors 44 and 46 assembled on top of the heat-conducting member 52 on each side of posts 40 and 42. Push-on speed nuts 48 and 50, mounted on posts 40 and 42, hold resistors 44 and 46 firmly against heat-conducting member 52 if used, and also hold the heat-conducting member firmly against the bottom walls of the lens holder wells 34 and 36. The resistors 44 and 46 are used as low cost heating elements. These resistors may have ceramic casings, and may be of the type designated PW22, manufactured by the International Resistance Corporation, a subsidiary of the TRW Company. Resistors 44 and 46 are connected in parallel, as shown in the circuit diagram of FIG. 6. These resistors may have a value of about 400 ohms each, when they are used in a unit suitable for use in conjunction with a 120-volt 60 Hz power line input.

Figure 6:
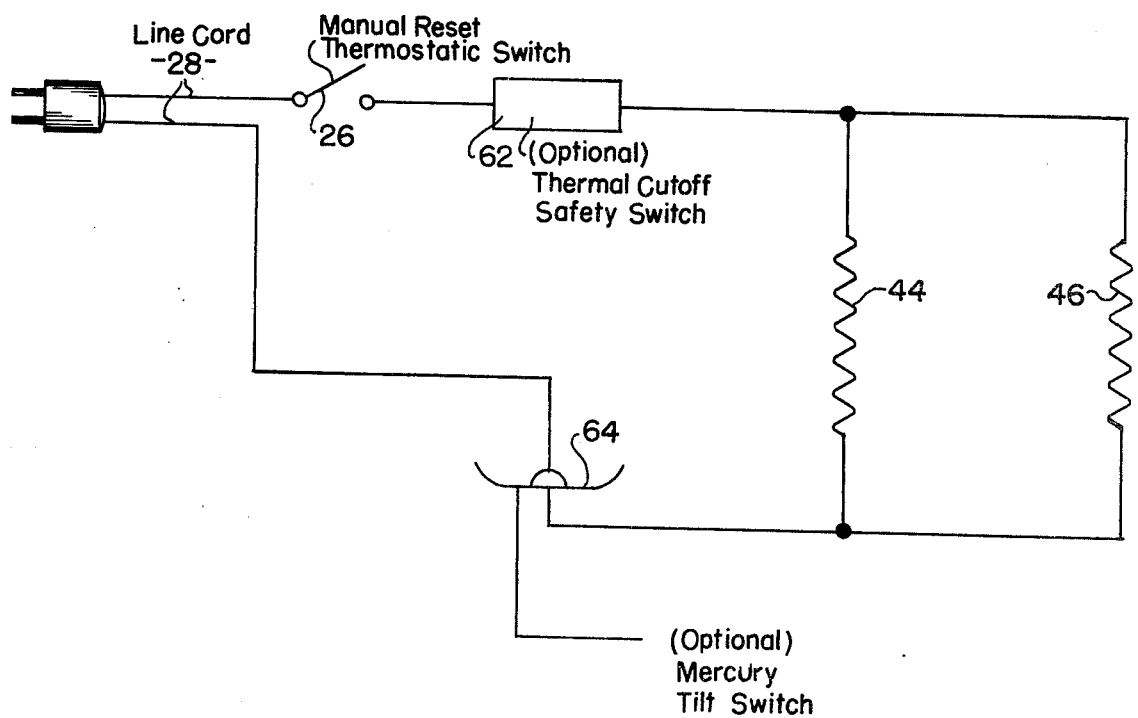
FIG. 6 is a circuit diagram representing the electrical connections within the heater unit.

The leads of resistors 44 and 46 extend through appropriate terminals into the switch cavity 24 of FIG. 3. The leads may be connected directly to switch 26, or through a thermal cut-off safety switch 62 (FIG. 6). Switch 62 opens permanently if excessive temperatures are reached with the unit. Likewise, a suitable mercury tilt switch 64 (FIG. 6) may be connected between resistors 44 and 46 and power cord 28, if it is desired to make the unit shut off automatically if it is tipped over.

Figure 2:
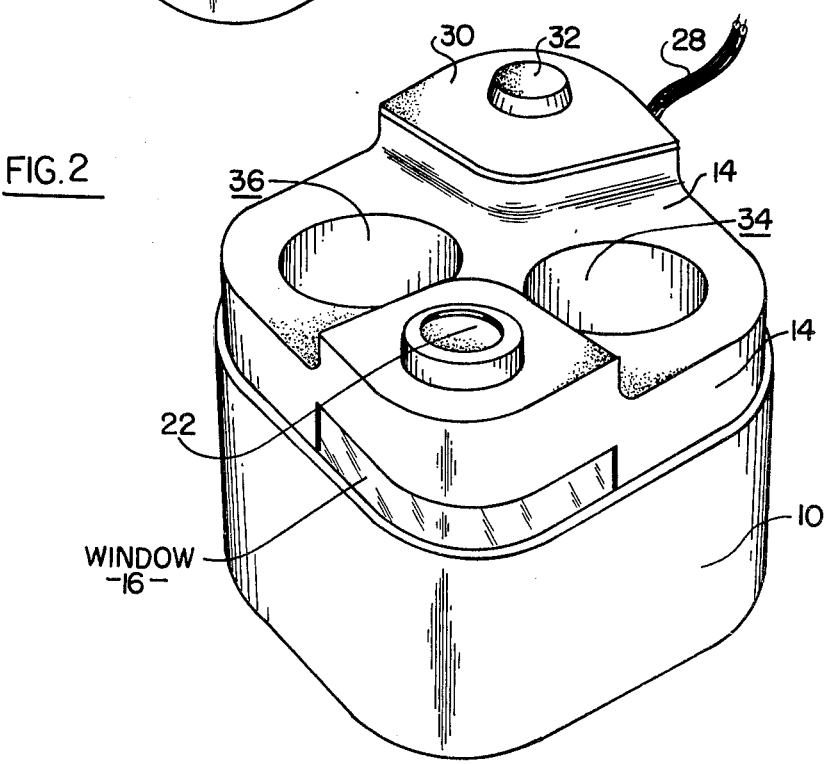
FIG. 2 is a perspective representation of the heating unit of FIG. 1 with the cover removed.

After the mechanical and electrical assembly of incubator 14 has been completed, the incubator is joined and sealed to the bowl 18 to form the sub-assembly shown in FIG. 3. The joining operation, preferably ultrasonic welding, forms an essentially hermetic seal between the two components. The top edge 18A of bowl 18 (FIG. 4) is welded to the flange area 58 of incubator 14 (FIG. 5) to form the seal. The sub-assembly of incubator 14 and bowl 18 is shown in FIGS. 2 and 3. The window 16 provides a means through which indicator 60 can be observed when the proper operating temperature has been reached, as will be described.

After the incubator and bowl have been sealed together, the unit is filled with a heat conducting liquid, such as a mixture of clear mineral oil and molten wax, for example, through the fill hole 20 of FIG. 3, at a temperature of approximately 100° C., to the level of the base of the fill hole 20. A plug 22 (FIG. 3) is now seated into the fill hole 20, and is sealed in place, preferably by ultrasonic welding, so as to provide a leak-tight containment for the oil and wax mixture. The wax preferably is a typical hydrocarbon paraffin wax available from major oil refineries. The wax may have its characteristics modified slightly by the addition of the clear mineral oil up to 20% by volume. The addition of mineral oil results in a whiter, more opaque appearing wax, when in its solid state.

The wax within the heating unit of the invention performs a number of functions. For example, when the unit is cold, at the start of a disinfection cycle, the wax is in a solid state. The solid wax is a white opaque material which is visible through window 16 of FIGS. 1 and 2. The opaque wax completely blocks the view through window 16 of indicator 60 of FIG. 4.

When the heating unit of the invention approaches its operating temperature in the disinfection cycle, the wax between window 16 and indicator 60 melts and becomes a water clear liquid. Indicator 60 is now readily visible through window 16 and through the molten wax. The combination of the wax, window 16 and indicator 60 provides, therefore, a positive indicator to the user when the proper disinfection temperatures have been reached.

As the unit cools down, after the disinfection cycle, the wax gradually returns to the solid white opaque state, and indicator 60 is no longer visible through window 16. When the indicator 60 is no longer visible, and the window 16 has returned to the view of the white wax, the user has a positive indication that the disinfection cycle has been completed, and that the lenses have been properly disinfected.

The wax within the unit also acts as a heat transfer medium. When the unit is cold, and when it is energized by depressing the manually activated thermostatic switch 26, the two resistors 44 and 46 begin to heat up. This action causes the solid wax adjacent the resistors to melt, and the melted liquid wax then begins to circulate by convection. The hot wax tends to rise, carrying heat to the unmelted wax toward the top of the unit by convection currents, as well as to the walls of the lens holder wells 34 and 36. Heat conducting member 52 of FIG. 5, if used, helps to control the heat distribution by aiding heating on the side of the wells 34 and 36 away from the heat pick-up 54 of FIG. 5.

The wax within the heating unit of the invention also acts as a temperature stabilization means since the latent heat of fusion of the wax is many times higher than the specific heat of the wax. This means that the molten wax tends to stay at the melting temperature of the wax as long as there is a reasonable amount of unmelted wax present. The heat produced by resistors 44 and 46 is largely used to supply the latent heat of fusion of the wax as it melts. The temperature of heat pick-up 54 will remain near the melting temperature of the wax as long as there is any unmelted wax in the vicinity.

After substantially all of the wax has been melted, no further heat input is required to supply the heat of fusion in melting the wax, and the temperature of the liquid wax will begin to rise above the melting temperature of the wax. When the molten wax reaches a predetermined temperature, heat pick-up member 54 conducts enough heat to raise the temperature of thermostatic switch 26 to its snap-off point. When that occurs, power is removed from the resistors and the heating unit begins to cool down. It should be noted that when thermostatic switch 26 is turned off, it remains off until it is manually reset.

The wax within the heating unit of the invention also provides a temperature stabilization action as the unit begins to cool down. As the molten wax begins to solidify, the latent heat of fushion used to melt the wax is returned by the wax. The temperature again tends to stabilize at the melting temperature of the wax until all of the wax is again solid.

The use of wax within the heating unit of the invention also permits the low cost resistors 44 and 46 to be used as heating elements. When the resistors are operated immersed in wax, the efficient convective heat transfer enables the wattage input to the resistors to be considerably higher than the rated wattage dissipation based on operation in free air. The allowable free air rating for the resistors is 22 watts, while operation in wax enables inputs of 40 watts to be used without exceeding the operating parameters of the resistors. It would, of course, be impractical to use such a low cost type of resistor to furnish heat to the lens holder wells were it not for the use of wax as the heat transfer medium.

The use of the wax in the heating unit of the invention, together with the mechanical and electrical components described above, results in a heating unit in which the temperature and time relationships of the unit are efficiently and positively controlled. Moreover, the use of wax in conjunction with the other components, permits the entire exterior of the heating unit to be constructed of injection molded plastic parts. This latter feature eliminates potential shock hazards, allowing the unit to be virtually hermetically sealed, to be readily cleanable for sanitary purposes, and to be low in manufacturing costs.

It will be appreciated that although a particular embodiment of the invention has been shown and described, modifications may be made. It is intended in the following claims to cover all the modifications which come within the true spirit and scope of the invention.

What is claimed is:

1. An electrically energized heating unit for disinfecting soft lenses, or the like, comprising: a housing; of plastic material a bowl formed of low heat conductive plastic material supported in the housing and providing an air space between the inner wall of the housing and the outer wall of the bowl which air space acts as an insulating means between the bowl and the housing; an incubator formed of low heat conductive plastic material supported on said bowl is sealed relationship therewith, said incubator containing at least one well extending into said bowl; electrically energized heating means mounted in said bowl; electric leads extending into said bowl for supplying electric energy to said heating means; a heat conductive wax contained in said bowl to be heated from a solid state to a liquid state by said heating means for conducting heat uniformly from said heating means to the outer surface of the well of said incubator so as to introduce heat into said well; and a thermostatic switch connected to said leads and thermally coupled to the wax in said bowl and having an operating temperature higher than the melting point of the wax in said bowl.

2. The electrically energized heating unit defined in claim 1, in which said electrical heating means comprises at least one electrical resistor mounted on the underside of said well to be immersed in said wax.

3. The electrically energizing heating unit defined in claim 1, in which said incubator includes a switching cavity; and in which said thermostatic switch is mounted in said cavity; and which includes a heat pick-up element for the switch mounted on the underside of the switch cavity to be immersed in said wax.

4. The electrically energized heating unit defined in claim 3, and which includes cover means for said switching cavity, said cover means including a sealed resilient means to permit manual resetting operation of the switch.

5. The electrically energized heating unit defined in claim 2, and which includes a heat conducting member mounted on the underside of said well adjacent to said resistor, said heat conducting member having a bent-over portion extending along the outer side of said well.

* * * * *